United States Patent
MacFarland et al.

(10) Patent No.: US 7,291,140 B2
(45) Date of Patent: Nov. 6, 2007

(54) SYSTEM AND METHOD FOR LOW AVERAGE POWER DERMATOLOGIC LIGHT TREATMENT DEVICE

(75) Inventors: Dean A. MacFarland, Magnolia, MA (US); Greg J. Spooner, Kensington, CA (US); Kevin P. Connors, San Francisco, CA (US); David A. Gollnick, San Francisco, CA (US)

(73) Assignee: Cutera, Inc., Brisbane, CA (US)

( * ) Notice: Subject to any disclaimer, the term of this patent is extended or adjusted under 35 U.S.C. 154(b) by 379 days.

(21) Appl. No.: 10/794,882

(22) Filed: Mar. 5, 2004

(65) Prior Publication Data

US 2004/0230260 A1    Nov. 18, 2004

Related U.S. Application Data

(60) Provisional application No. 60/456,848, filed on Mar. 21, 2003, provisional application No. 60/488,252, filed on Jul. 18, 2003.

(51) Int. Cl.
*A61N 18/18* (2006.01)

(52) U.S. Cl. .................. 606/9; 128/898; 606/13

(58) Field of Classification Search ........... 128/898; 606/9; 607/88–94
See application file for complete search history.

(56) References Cited

U.S. PATENT DOCUMENTS

| | | | |
|---|---|---|---|
| 634,113 A | 3/1950 | Riley | |
| 2,699,771 A | 1/1955 | Rüttger-Pelli | 128/24.1 |
| 3,327,712 A | 6/1967 | Kaufman | 128/398 |
| 3,538,919 A | 11/1970 | Meyer | 606/36 |
| 3,648,706 A | 3/1972 | Holzer | 128/395 |
| 3,693,623 A | 9/1972 | Harte et al. | 128/303.1 |
| 3,834,391 A | 9/1974 | Block | 606/9 |
| 3,867,948 A | 2/1975 | Kellenbom | 128/395 |

(Continued)

FOREIGN PATENT DOCUMENTS

CA    968854    6/1975    ........... 326/4

(Continued)

OTHER PUBLICATIONS

R.M. Adrian, "Treatment of Facial Telangiectasia Using the VersaPulse® Variable Pulse Width Frequency Doubled Neodymium:YAG Laser: A Case Report," 2 pages in length.

(Continued)

*Primary Examiner*—Henry M Johnson, III
(74) *Attorney, Agent, or Firm*—Stallman & Pollock LLP

(57) ABSTRACT

The invention comprises a system and method for providing for pulses or relatively low energy light to an area of skin being treated. Typically, these low energy pulses will include shorter wavelength light, and will provided for multiple pulses of light for the area being treated. The pulse width is determined by the characteristics of a storage capacitor and the flashlamp. The overall system design can be relatively simple, and the operation of such a system can allow for operation by relatively inexperienced users. Due to the low energy pulse, it can be necessary to apply a greater overall amount of energy per treatment area relative to other previous systems, but due to the relatively long period of time between pulses the operation is such that risk of injury is significantly reduced relative to prior systems.

8 Claims, 4 Drawing Sheets

U.S. PATENT DOCUMENTS

| | | | | |
|---|---|---|---|---|
| 3,900,034 A | 8/1975 | Katz et al. ................... 607/89 |
| 4,020,383 A | 4/1977 | Labadini et al. ............ 313/344 |
| 4,022,534 A | 5/1977 | Kishner ...................... 356/210 |
| 4,122,853 A | 10/1978 | Smith ............................. 606/4 |
| 4,233,493 A | 11/1980 | Nath ........................... 219/354 |
| 4,298,005 A | 11/1981 | Mutzhas ..................... 128/395 |
| 4,388,924 A | 6/1983 | Weissman et al. ............. 606/9 |
| 4,461,294 A | 7/1984 | Baron ............................ 606/5 |
| 4,505,545 A | 3/1985 | Salia-Munoz ............... 350/321 |
| 4,539,987 A | 9/1985 | Nath et al. ................ 128/303.1 |
| 4,608,978 A | 9/1986 | Rohr ......................... 128/303.1 |
| 4,608,990 A | 9/1986 | Elings ......................... 128/633 |
| 4,617,926 A | 10/1986 | Sutton ........................... 606/9 |
| 4,658,823 A | 4/1987 | Beddoe et al. .............. 128/396 |
| 4,667,658 A | 5/1987 | Guibert ..................... 128/24.1 |
| 4,686,986 A | 8/1987 | Fenyö et al. ................ 128/396 |
| 4,733,660 A | 3/1988 | Itzkan ............................ 606/9 |
| 4,747,660 A | 5/1988 | Nishioka et al. ......... 350/96.25 |
| 4,757,431 A | 7/1988 | Cross et al. ................ 362/261 |
| 4,784,135 A | 11/1988 | Blum et al. ............... 128/303.1 |
| 4,813,412 A | 3/1989 | Yamazaki et al. ...... 128/303.13 |
| 4,819,669 A | 4/1989 | Politzer ...................... 132/200 |
| 4,829,262 A | 5/1989 | Furumoto ................... 330/4.3 |
| 4,860,172 A | 8/1989 | Schlager et al. .............. 362/32 |
| 4,884,568 A | 12/1989 | Hahn ........................ 128/303.1 |
| 4,917,084 A | 4/1990 | Sinofsky ........................ 606/7 |
| 4,930,504 A | 6/1990 | Diamantopoulos et al. . 128/395 |
| 4,950,880 A | 8/1990 | Hayner ..................... 250/201.9 |
| 4,976,709 A | 12/1990 | Sand .............................. 606/5 |
| 5,000,752 A | 3/1991 | Hoskin et al. .................. 606/9 |
| 5,057,104 A | 10/1991 | Chess ............................. 606/9 |
| 5,059,192 A | 10/1991 | Zaias .............................. 606/9 |
| 5,139,494 A | 8/1992 | Freiberg ........................ 606/3 |
| 5,161,526 A | 11/1992 | Hellwing et al. ........... 128/395 |
| 5,182,857 A | 2/1993 | Simon ....................... 30/34.05 |
| 5,207,671 A | 5/1993 | Franken et al. ................ 606/9 |
| 5,217,455 A | 6/1993 | Tan ................................ 606/9 |
| 5,226,907 A | 7/1993 | Tankovich ................. 606/133 |
| 5,258,989 A | 11/1993 | Raven ............................ 372/6 |
| 5,259,380 A | 11/1993 | Mendes et al. ............. 607/115 |
| 5,282,797 A | 2/1994 | Chess ............................. 606/9 |
| 5,290,273 A | 3/1994 | Tan ................................ 606/9 |
| 5,304,169 A | 4/1994 | Sand .............................. 606/5 |
| 5,304,170 A | 4/1994 | Green ............................ 606/9 |
| 5,312,395 A | 5/1994 | Tan et al. ....................... 606/9 |
| 5,320,618 A | 6/1994 | Gustafsson .................... 606/9 |
| 5,336,217 A | 8/1994 | Buys et al. ..................... 606/9 |
| 5,337,741 A | 8/1994 | Diamond ....................... 600/8 |
| 5,344,418 A | 9/1994 | Ghaffari ........................ 606/9 |
| 5,344,434 A | 9/1994 | Talmore ..................... 607/88 |
| 5,397,327 A | 3/1995 | Koop et al. .................. 606/17 |
| 5,405,368 A | 4/1995 | Eckhouse ................... 607/88 |
| 5,409,479 A | 4/1995 | Dew et al. ..................... 606/9 |
| 5,425,728 A | 6/1995 | Tankovich ..................... 606/9 |
| 5,441,531 A | 8/1995 | Zarate et al. ................ 607/90 |
| 5,458,596 A | 10/1995 | Lax et al. ..................... 606/31 |
| 5,474,549 A | 12/1995 | Ortiz et al. ..................... 606/9 |
| 5,486,172 A | 1/1996 | Chess ........................... 606/20 |
| 5,511,563 A | 4/1996 | Diamond ..................... 128/848 |
| 5,522,813 A | 6/1996 | Trelles ........................... 606/2 |
| 5,527,350 A | 6/1996 | Grove et al. ................ 607/89 |
| 5,569,979 A | 10/1996 | Scott et al. .................. 313/636 |
| 5,572,091 A | 11/1996 | Langer et al. .............. 313/636 |
| 5,591,157 A | 1/1997 | Hennings et al. .............. 606/3 |
| 5,595,568 A | 1/1997 | Anderson et al. .............. 606/9 |
| 5,611,795 A | 3/1997 | Slatkine et al. ................. 606/9 |
| 5,620,478 A | 4/1997 | Eckhouse ................... 607/88 |
| 5,660,836 A | 8/1997 | Knowlton ................... 424/400 |
| 5,683,380 A | 11/1997 | Eckhouse et al. .............. 606/9 |
| 5,725,522 A * | 3/1998 | Sinofsky ........................ 606/8 |
| 5,735,844 A | 4/1998 | Anderson et al. .............. 606/9 |
| 5,755,753 A | 5/1998 | Knowlton ................... 607/98 |
| 5,769,844 A | 6/1998 | Ghaffari ...................... 606/16 |
| 5,769,878 A | 6/1998 | Kamei ........................ 607/88 |
| 5,782,895 A | 7/1998 | Zarate et al. ................ 607/88 |
| 5,807,261 A | 9/1998 | Benaron et al. ............. 600/473 |
| 5,810,801 A | 9/1998 | Anderson et al. .............. 606/9 |
| 5,814,040 A | 9/1998 | Nelson et al. .................. 606/9 |
| 5,820,625 A | 10/1998 | Izawa et al. .................... 606/9 |
| 5,830,208 A | 11/1998 | Muller ........................... 606/9 |
| 5,843,074 A | 12/1998 | Cocilovo ..................... 606/10 |
| 5,843,143 A | 12/1998 | Whitehurst ................. 607/88 |
| 5,885,274 A | 3/1999 | Fullmer et al. ................. 606/9 |
| 5,919,219 A | 7/1999 | Knowlton ................... 607/102 |
| 5,964,749 A | 10/1999 | Eckhouse et al. .............. 606/9 |
| 5,989,283 A | 11/1999 | Wilkens ..................... 607/88 |
| 6,015,404 A | 1/2000 | Altshuler et al. ............... 606/9 |
| 6,050,990 A | 4/2000 | Tankovich et al. ............. 606/9 |
| 6,080,146 A | 6/2000 | Altshuler et al. ............... 606/9 |
| 6,080,147 A | 6/2000 | Tobinick ........................ 606/9 |
| 6,096,066 A | 8/2000 | Chen et al. .................. 607/88 |
| 6,120,497 A | 9/2000 | Anderson et al. .............. 606/9 |
| 6,168,590 B1 | 1/2001 | Neev .............................. 606/9 |
| 6,171,332 B1 | 1/2001 | Whitehurst ................. 607/89 |
| 6,228,074 B1 | 5/2001 | Almeida ......................... 606/9 |
| 6,235,015 B1 | 5/2001 | Mead, III et al. .............. 606/9 |
| 6,241,753 B1 | 6/2001 | Knowlton ................... 607/99 |
| 6,273,884 B1 | 8/2001 | Altshuler et al. ............... 606/9 |
| 6,280,438 B1 | 8/2001 | Eckhouse et al. .............. 606/9 |
| 6,319,273 B1 | 11/2001 | Chen et al. .................. 607/88 |
| 6,374,265 B1 | 4/2002 | Chen et al. .................... 606/5 |
| 6,377,855 B1 | 4/2002 | Knowlton ................... 607/101 |
| 6,381,498 B1 | 4/2002 | Knowlton ................... 607/101 |
| 6,383,176 B1 | 5/2002 | Connors et al. ................ 606/9 |
| 6,387,089 B1 | 5/2002 | Kreindel et al. ............... 606/9 |
| 6,405,090 B1 | 6/2002 | Knowlton ................... 607/102 |
| 6,413,253 B1 | 7/2002 | Koop et al. .................. 606/27 |
| 6,443,978 B1 | 9/2002 | Zharov ........................ 607/91 |
| 6,453,202 B1 | 9/2002 | Knowlton ................... 607/102 |
| 6,461,866 B1 | 10/2002 | Whitehurst ................. 435/325 |
| 6,482,199 B1 | 11/2002 | Neev ............................ 606/10 |
| 6,485,484 B1 | 11/2002 | Connors et al. ................ 606/9 |
| 6,508,813 B1 | 1/2003 | Altshuler ........................ 606/9 |
| 6,511,475 B1 | 1/2003 | Altshuler et al. ............... 606/9 |
| 6,517,532 B1 | 2/2003 | Altshuler et al. ............... 606/9 |
| 6,524,329 B1 | 2/2003 | Benedict .................... 607/88 |
| 6,558,372 B1 | 5/2003 | Altshuler ........................ 606/2 |
| 6,569,155 B1 | 5/2003 | Connors et al. ................ 606/9 |
| 6,595,986 B2 * | 7/2003 | Almeida ......................... 606/9 |
| 6,602,275 B1 | 8/2003 | Sullivan ..................... 607/88 |
| 6,605,080 B1 | 8/2003 | Altshuler et al. ............... 606/3 |
| 6,648,904 B2 | 11/2003 | Altshuler et al. ............. 607/96 |
| 6,653,618 B2 | 11/2003 | Zenzie ....................... 250/221 |
| 6,663,620 B2 | 12/2003 | Altshuler et al. ............... 606/9 |
| 6,663,659 B2 * | 12/2003 | McDaniel ................... 607/88 |
| 6,723,090 B2 | 4/2004 | Altshuler et al. ............... 606/9 |
| 6,730,113 B2 * | 5/2004 | Eckhardt et al. ............. 607/94 |
| 6,743,222 B2 | 6/2004 | Durkin et al. .................. 606/9 |
| 6,749,624 B2 | 6/2004 | Knowlton ................... 607/104 |
| 6,981,970 B2 * | 1/2006 | Karni ............................ 606/9 |
| 2001/0051766 A1 * | 12/2001 | Gazdzinski ................ 600/309 |
| 2002/0055092 A1 | 5/2002 | Hochman ....................... 435/4 |
| 2002/0091377 A1 | 7/2002 | Anderson et al. .............. 606/9 |
| 2002/0128635 A1 | 9/2002 | Altshuler et al. ............... 606/9 |
| 2002/0161357 A1 | 10/2002 | Anderson et al. .............. 606/9 |
| 2002/0173780 A1 | 11/2002 | Altshuler et al. ............... 606/9 |
| 2002/0198575 A1 | 12/2002 | Sullivan ..................... 607/88 |
| 2003/0004499 A1 | 1/2003 | McDaniel ....................... 606/3 |
| 2003/0004501 A1 * | 1/2003 | Wilkens et al. ................ 606/9 |
| 2003/0004556 A1 * | 1/2003 | McDaniel ................... 607/88 |
| 2003/0023283 A1 | 1/2003 | McDaniel ................... 607/88 |
| 2003/0032900 A1 | 2/2003 | Ella .............................. 601/6 |
| 2003/0032950 A1 | 2/2003 | Altshuler et al. ............... 606/9 |
| 2003/0045916 A1 | 3/2003 | Anderson et al. ............ 607/89 |

| | | | | |
|---|---|---|---|---|
| 2003/0055413 | A1 | 3/2003 | Altshuler et al. | 606/9 |
| 2003/0055414 | A1 | 3/2003 | Altshuler et al. | 606/9 |
| 2003/0057875 | A1 | 3/2003 | Inochkin et al. | 351/224 |
| 2003/0065313 | A1 | 4/2003 | Koop et al. | 606/9 |
| 2003/0065314 | A1 | 4/2003 | Altshuler et al. | 606/9 |
| 2003/0125788 | A1 | 7/2003 | Long | 607/133 |
| 2003/0130709 | A1 | 7/2003 | Haber et al. | 607/88 |
| 2003/0195494 | A1 | 10/2003 | Altshuler et al. | 606/9 |
| 2003/0199859 | A1 | 10/2003 | Altshuler et al. | 606/9 |
| 2004/0010298 | A1 | 1/2004 | Altshuler et al. | 607/88 |
| 2004/0024388 | A1 | 2/2004 | Altshuler | 606/2 |
| 2004/0034319 | A1 | 2/2004 | Anderson et al. | 604/20 |
| 2004/0092916 | A1* | 5/2004 | Jay | 606/9 |
| 2004/0093042 | A1 | 5/2004 | Altshuler et al. | 607/88 |
| 2004/0147985 | A1 | 7/2004 | MacFarland et al. | 607/90 |
| 2004/0147986 | A1* | 7/2004 | Baumgardner et al. | 607/94 |
| 2005/0085878 | A1* | 4/2005 | Wilkens et al. | 607/94 |

FOREIGN PATENT DOCUMENTS

| | | | |
|---|---|---|---|
| CA | 1041610 | 10/1978 | 326/6 |
| DE | 33 47 730 A1 | 7/1985 | |
| DE | 39 06 860 A1 | 9/1989 | |
| EP | 0 565 331 A2 | 4/1993 | |
| GB | 2 360 946 A | 10/2001 | |
| JP | 4-98795 | 3/1992 | |
| WO | WO 86/02783 | 5/1986 | |
| WO | WO 89/00871 | 2/1989 | |
| WO | WO 95/15725 | 6/1995 | |
| WO | WO 96/22813 | 8/1996 | |
| WO | WO 97/37723 | 10/1997 | |
| WO | WO 98/24514 | 6/1998 | |
| WO | WO 98/38933 | 9/1998 | |
| WO | WO 98/51235 | 11/1998 | |
| WO | WO 99/07438 | 2/1999 | |
| WO | WO 99/11324 | 3/1999 | |
| WO | WO 00/54685 | 9/2000 | |
| WO | WO 00/54685 A3 | 9/2000 | |

OTHER PUBLICATIONS

J.C. Allain et al., "Isometric Tensions Developed During the Hydrothermal Swelling of Rat Skin," *Connective Tissue Research*, vol. 7, pp. 127-133 (1980).

R.R. Anderson, "Clinical Use of the Lightsheer Diode Laser System," (reprinted with permission from Harvard Medical School, Mar. 1998) from the website located at http://www.lasertraining.com/med-8.htm, printed Sep. 15, 1998, 5 pages long.

R.R. Anderson et al., *International Advances in Sugical Oncology* (vol. 5), section entitled "Lasers in Dermatology Provide a Model for Exposing New Applications in Surgical Oncology," publisher Alan R. Liss, Inc. (1982), pp. 341-358.

R.R. Anderson, Brochure by Palomar Medical Technologies, Inc., "A Clinical Study on Ruby Lasers for Permanent Hair Reduction," 8 pages in length (1999).

R.R. Anderson, "Safety and Efficacy of the Palomar Ruby Laser for Hair Removal," Harvard Medical School, Mar. 1997, 2 pages in length.

R.R. Anderson, "Hair Removal Using Light," Harvard Medical School, Mar. 1997, 2 pages in length.

R.R. Anderson, "Clinical Use of the EpiLaser® System," 8 pages in length (1998).

G.B. Bartley et al., "An Experimental Study to Compare Methods of Eyelash Ablation," *Opthamology*, vol. 94, pp. 1286-1289 (1987).

J.-L. Boulnois, "Photophysical Processes in Recent Medical Laser Developments: a Review," *Laser in Medical Science*, vol. 1, pp. 47-64 (1986).

Brochure, from Laser Aesthetics, Inc., "The Cool Touch Laser," one page in length.

C. Chess et al., "Cool Laser Optics Treatment of Large Telangiectasia of the Lower Extremities," *J. Dermatol. Surg. Oncol.*, vol. 19, pp. 74-80 (1993).

W.F. Coulson et al., "Nonblative Laser Treatment of Facial Rhytides: Animal Study," *Abstract of BiOS '98 Symposium [Cutaneus Applications of Lasers]*, Jan. 24-30, 1998 in San Jose, CA, one page in length.

C.C. Danielsen, "Age-related thermal stability and susceptibility to proteolysis of rat bone collagen," *Biochem J.*, vol. 272, No. 3, Dec. 15, 1990, pp. 697-701.

C.C. Danielsen, Thermal Stability of Reconstituted Collagen Fibrils, Shrinkage Characteristics upon In Vitro Maturation, *Mechanisms of Ageing and Development*, vol. 15, pp. 269-278 (1981).

J.S. Dover et al., "Pigmented Guinea Pig Skin Irradiated With Q-Switched Ruby Laser Pulses," *Arch. Dermatol.*, vol. 125, Jan. 1989, pp. 43-49.

L.H. Finkelstein et al., "Epilation of Hair-Bearing Urethral Grafts Using the Neodymium: YAG Sugical Laser," *J. Urology*, vol. 146, pp. 840-842 (1991).

R. Fitzpatrick, "Treatment of Wrinkles with the UltraPulse $CO_2$ Laser," 3 pages in length.

L. Goldman, "Comparison of the Biomedical Effects of the Exposure of Human Tissues to Low and High Energy Lasers," *Ann. N.Y. Acad. Sci.*, vol. 122, May 2, 1965, pp. 802-833.

"Laser Sugery of Angiomas with Special Reference to Port-Wine Angiomas," *AMA Association*, Jun. 18-22, 1967, 8 pages in length.

J.M. Grevelink et al., "Clinical and Histological Responses of Congenital Melanocytic Nevi After Single Treatment With Q-Switched Lasers," *Arch. Dermatol.*, vol. 133, Mar. 1997, pp. 349-353.

M.D. Grossman, et al., "Prospective Evaluation of the Argon Laser in the Treatment of Trichiasis," *Opthalmic Surgery*, vol. 23, pp. 183-187 (1992).

M.D. Grossman et al., "Experimental Comparison of Laser and Cryosurgical Cilia Destruction," *Opthalmic Surgery*, vol. 23, pp. 179-182 (1992).

K. Kincade, "Demand for Laser Resurfacing Soars," *Dermatology Times*, vol. 16, No. 10, Oct. 1995, 4 pages in length.

P, Kronick et al., "The Locations of Collagens with Different Thermal Stabilities in Fibrils of Bovine Reticular Dermis," *Connective Tissue Research*, vol. 18, pp. 123-134 (1988).

H. Kubota et al., "Atrial Ablation With an IRK-151 Infrared Coagulator," *Ann. Thoracic Surg.*, vol. 66, pp. 95-100 (1998).

J.G. Kuhns et al., "Laser Injury in Skin," *Laboratory Investigations*, vol. 17, No. 1, pp. 1-13 (1967).

D.B. Kuriloff et al., "Pharyngoesophageal hair growth: The role of laser epilation," *Case Reports*, vol. 98, pp. 342-345 (1988).

J.R. Lloyd et al., "Selective Photothermolysis of the Sebaceous Gland for Acne Treatment," *Laser in Surgery and Medicine*, vol. 31, pp. 115-120 (2002).

M.A. Mainster, "Ophthalmic applications of infrared lasers-thermal considerations," *Invest Opthalmal. Visual Sci*, vol. 18, No. 4, Apr. 1979, pp. 414-420.

T. Matsumoto et al., "Ruby Laser Treatment of Melanin Pigmented Skin Lesions using Toshiba Model LRT—301A Ruby Laser," *Journal of the Japanese Society for Laser Surgery and Medicine*, vol. 10, No. 3, Dec. 1989, pp. 451-454.

J.B. Murdoch, *Illumination Engineering—From Edison's Lamp to the Laser*, Chapt. 6.8 entitled "Tungsten-Halogen Lamps," published by Macmillan Publishing Company (1985), pp. 208-211.

M.H. Niemz, *Laser-Tissue Interactions Fundamentals and Applications*, Chapt. 3.2.3 entitled "Heat Effects," published by Springer-Verlag Berlin Heidelberg (1996), pp. 77-80.

T. Ohshiro, et al., "The Ruby and Argon Lasers in the Treatment of Naevi," *Annals Academy of Medicine*, vol. 12, No. 2 (Suppl.), Apr. 1983), 8 pages in length.

T. Ohshiro, "Treatment by Ruby Laser Beams in the Field of Dermatology," "*Japan Medical News*," Separate Volume No. 2768, issued on May 14, 1997, 21 pages in length (English translation attached).

H. Ohtsuka et al., "Ru Laser Histological Studies and Clinical Experiences of Ruby Laser Treatment," 9 pages in length (1991) (1st page is an English Abstract).

I. Ono et al., "Histopathological Alteration of Skin and Irradiation of Rudy Laser," *Journal of Japanese Society for Laser Surgery and Medicine*, vol. 11, No. 4, Mar. 4, 1991, 2 pages in length (1st page is an English abstract).

D.Y. Paithankar et al., "Acne Treatment With a 1,450 nm Wavelength Laser and Cryogen Spray Cooling," *Lasers in Surgery and Medicine*, vol. 31, pp. 106-114 (2002).

J.A. Pearce et al., "Kinetic Models of Laser-Tissue Fusion Processes," *Biomed. Sci. Instrum.*, vol. 39, pp. 355-360 (1993).

L.L. Polla et al., "Melanosomes Are a Primary Target of Q-Switched Ruby Laser Irradiation in Guinea Pig Skin," *The Journal of Investigative Dermatology*, vo. 89, No. 3, Sep. 1987, pp. 281-286.

Press Release, "New Laser Eliminates 'Lipstick Bleed,'" 3 pages in length.

J. Ruiz-Esparza et al., "Nonblative Radiofrequency for Active Acne Vulgaris: The use of Deep Dermal Heat in the Treatment of Moderate to Severe Active Acne Vulgaris (Thermotherapy): A Report of 22 Patients," *Dermatol Surg.*, vol. 29, No. 4, Apr. 2003, pp. 333-339.

Spectrum Medical Technologies, Inc., an operator's manual written by Lasermetrics, Inc., exclusively for Spectrum Medical Technologies, Inc., Q-Switched Ruby Laser System Model RD-1200, 23 pages in length.

E.R. Squibb & Sons, "Laser Light the Way to New Research Concepts in Science Industry Medicine," 33 pages in length.

R. Tanino et al., "Development of Ruby Laser System for Medical Use," *Journal of the Japanese Society for Laser Surgery and Medicine*, vol. 11, No. 4, Mar. 4, 1991, pp. 93-98.

Iwasaki et al., (Abstract) "Development of Laser Systems for Treatment of Hyperpigmented Skin Lesions," *Publication unknown—entire article is in Japanese except for the Abstract*, revised Mar. 1, 1989, pp. 26-34 (Abstract appears on p. 34).

Brochure by Palomar EsteLux™, "Pulsed-Light System," website http://www.palmed.com/laser_estelux.html, printed Jul. 15, 2003, 3 pages in length.

Brochure by Sciton, "PROFILE™ Combination Long Pulse Erbium and Long Pulse Nd:YAG 1064," website http://www.sciton.com/public/profile.htm, printed Jul. 15, 2003, 2 pages in length.

Brochure by Lumenis Aesthetic, "VascuLight™ The World's Most Versatile System for Aesthetic Procedures," website http://www.aesthetic.lumenis.com/wt/content/vasculaight, printed Jul. 15, 2003, 2 pages in length.

Brochure by Lumenis, "VASCU*Light*™ ELITE [Versatility and Speed for the Ultimate Aesthetic System]," Copyright 2002, the Lumenis group of companies, 2 pages in length.

Brochure by Lumenis, "VASCU*Light*™ VS [Versatility and Speed for the Ultimate Aesthetic System]," Copyright 2002, the Lumenis group of companies, 2 pages in length.

Brochure by Lumenis, "VASCU*Light*™ SR [Versatility and Speed for the Ultimate Aesthetic System]," Copyright 2002, the Lumenis group of companies, 2 pages in length.

In re U.S. Appl. No. 60/363,871, filed Mar. 12, 2002, by R. Rox Anderson et al., entitled "Method and Apparatus for Hair Growth Control," 20 pages in length.

* cited by examiner

SYSTEM AND METHOD FOR LOW AVERAGE POWER DERMATOLOGIC LIGHT TREATMENT DEVICE

RELATED APPLICATIONS

The present application claims benefit from U.S. Provisional Patent Application Ser. No. 60/456,848, Mar. 21, 2003, entitled SYSTEM AND METHOD FOR LOW AVERAGE DERMATOLOGIC LIGHT TREATMENT DEVICE, which is incorporated herein by reference. The present application also claims benefit from U.S. Provisional Patent Application Ser. No. 60/488,252, Jul. 18, 2003, entitled SYSTEM AND METHOD FOR LOW AVERAGE POWER DERMATOLOGIC LIGHT TREATMENT DEVICE, which is incorporated herein by reference.

BACKGROUND

Pulsed light provided by sources such as flashlamps and lasers have been used for several years for the removal of unwanted hair, and for treatments such as removal of pigmentation or vascular lesions.

Pulsed light sources may act through a number of mechanisms, including photomechanical disruption, photothermal ablation, photochemical ablation and photothermal coagulation/denaturation. Some of these light sources act by purely non-thermal means (i.e. mode-locked or Q-switched short pulse lasers) and others use a thermal effect to produce ablation or disruption of tissue. The most widely used and successful light sources for depilation or removal of pigmented and vascular lesions employ a photothermal interaction in which the mechanism of action is pulsed light used to locally heat the lesion or hair follicle with one or more closely spaced pulses in order to raise the temperature of the targeted tissue during or immediately following a single pulse to a temperature which will cause the death, damage, or reduced function, or reduced viability of the targeted tissue. The higher absorption of the target tissue will elevate its temperature with respect to the surrounding tissue, resulting in selective thermal destruction of the lesion or follicle, while the surrounding tissue will not be raised to a temperature which causes thermal destruction. Prior devices relied on relatively high power pulses of light (electromagnetic radiation) from a light source, such as a laser or a flashlamp. For example, typical prior devices provide energy pulses in the range of 10-40 $J/cm^2$ for a treatment provided to a selected area. Some of these prior devices provide for supplying a single pulse providing the treatment energy. Other prior devices utilize a series of closely spaced lower energy pulses, where the frequency of the pulses may be in the range of 10 hz or higher, which corresponds to a time between pulses of 100 ms or less. FIG. 1 shows part of a series of pulses which generally represents a pulse treatment which would be provided using a typical system and method of prior thermal treatment devices. As shown in FIG. 1 a period between pulses T is provided. Depending on the particular system this might range from 1 ms, or slightly less, to as much as 100 ms for treating hair follicles or treatment of skin pigmentation. The pulse width PW would typically be in the range of 2-5 ms. In applications for the treatment of skin pigmentation and removal of hair follicles, and for applications utilizing a flashlamp, the period between pulses was typically far less than 100 ms between pulses. In many other applications, for example, treatments for the removal of melanin-bearing sun damaged spots on skin, the treatment times may be as short as 5 ms, or even shorter.

One issue with present systems is that because a relatively large amount of fluence and power applied to the skin, an incorrect setting in terms of the fluence or time of treatment can cause unwanted results, and in some cases can result in scarring, hypopigmentation or hyperpigmentation. For example, consider a situation in which a fluence of 40 $J/cm^2$ is delivered to a treatment area during a 10 ms pulse width, the peak intensity for this treatment would be 4,000 $W/cm^2$. Because the treatment time is so short, there is a possibility that a patient would receive too much energy in too short of a time period which could result in a treatment area receiving an excess amount of energy and might cause unwanted damage to the tissue. Further, because the treatment energy is applied over such a short time period, the patient's natural pain reflex may not be fast enough to allow a patient to discontinue the treatment, prior to severe overheating of the tissue. Thus, these prior systems typically require trained and qualified medical personnel to apply the treatment. Such devices are therefore not safely or reasonably used directly by a patient or consumer.

Another issue with present systems is that they require relatively complex and expensive power supplies. This is because the appropriate energy must be delivered over a very short time, necessitating a highly rated high voltage power supply. In the past, the complexity of the power supply required that the power supply be housed in a module which was separated from the treatment device housing the flashlamp that provides light energy to the treatment area.

Additionally, because of the high treatment power used in prior systems, these systems must provide for a relatively sophisticated cooling system for keeping the temperature of critical system components sufficiently low, so that the energy being dissipated over a short time period will not cause the application device to become overheated.

DETAILED DESCRIPTION

Figure 1:
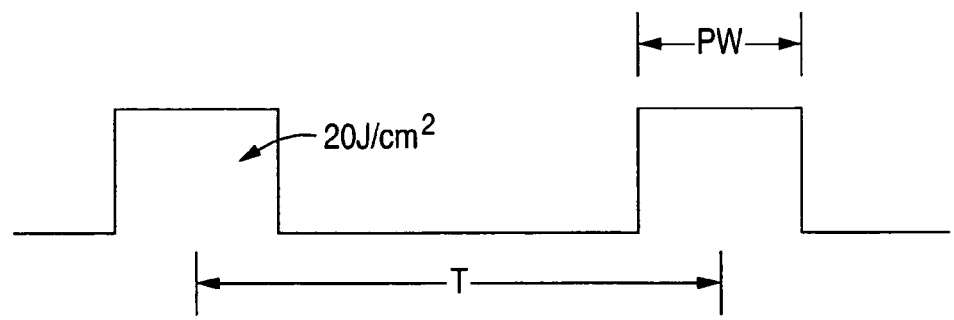
FIG. 1 shows light treatment pulses of the prior art.

The systems and methods herein provide a different approach for using light to provide dermatologic treatments. Instead of using one pulse, or a series of closely spaced pulses, to provide a high amount of energy to a treatment area over a short amount time, the system and method herein deliver an amount of energy necessary for a treatment over a relatively long time period. As with prior systems, the system herein can be used to treat unwanted hair follicles, and to treat pigmentation and vascular lesions.

The system herein provides for a series of relatively low energy pulses, which provides a lower rate of temperature rise of target tissue than in prior systems. It has been recognized by the inventors herein that this lower rate temperature rise can provide an effective method for treatment of follicles and pigment. In fact, the temperature rise of targeted tissue by low energy pulse exposures can fall into at least three classes:

(1) a relatively high fluence that produces melanin-bearing or follicular cell death, resulting in reduction of pigmented lesions or hair. The approximate range of the fluence per shot is ~3-6 J/cm$^2$. The time period of each pulse would be in range of 0.1-2 ms. The time period between each pulse would be in the range of 0.5-3.0 sec.
(2) low fluences that arrest, stunt or retard follicular growth. This range is approximately 1-3 J/cm$^2$. Pigment removal or destruction does not happen in this range. The time period of each pulse would be in range of 0.1-2 ms. The time period between each pulse would be in the range of 0.3-3.0 sec.
(3) Very low fluences that prevent follicles from re-emerging from an arrested state. In this case the exposure levels may be less than 1 J/cm$^2$. The time period of each pulse would be in range of 0.1-2 ms. The time period between each pulse would be in the range of 0.1-3.0 sec.

The system and method use an approach of stacking or delivering multiple low power pulses on a treatment area over a relatively long period of time. The total fluence required to reach the desired treatment effect on the tissue may be larger than in existing methods. However, the economy and reduction in system complexity resulting from the delivery of many smaller, lower fluence pulses, rather than a smaller number of larger fluence pulses, is significant. In addition, a lower fluence, multipulse treatment may be a less painful treatment than single pulse treatments.

In some prior small air cooled systems a major cost is in the circuitry and components necessary to provide electrical pulses to drive the flashlamp to provide relatively high energy per pulse (12-60 j/cm$^2$). Utilizing a method which provides for a treatment with lower energy pulses (1-6 j/cm$^2$) allows for the development of significantly different systems for providing thermal treatments. One area where significant cost savings can be realized is in the capacitor bank that is used in the high voltage power supply of the system, and in other components of the power supply.

The present system also utilizes longer time intervals spacing between pulses which further allows for providing a power supply with reduced demands on the capacitor bank which is discharged through the flashlamp. An embodiment of the present system provides a power in a range from 0.5 to tens of watts of average power per square cm of treatment spot size. This contrasts with some prior systems which provide for power in the range of hundereds to thousands of watts per square cm of treatment area. In one embodiment of the present system pulses are separated by at least 0.1 seconds which allows for unassisted cooling or thermal relaxation of the skin between the successive pulses. In one embodiment treatments will provide for between 2 to 20 pulses per spot.

Another aspect of an embodiment of the invention is the contact detector. This is a switch which detects the contact of the treatment window with the skin. If the window is not in contact with the skin a treatment pulse will not be delivered. The contact switch may be a mechanical switch or a capacitive sensing switch or a switch that detects the resistance change when electrodes are applied to skin. Another implementation may use an optical detector to sense the presence of skin at the treatment aperture. This will result in enhanced eye safety where the device by only allowing firing when the window is contacting a surface.

Another aspect of an embodiment of the invention is the pulse formatting. The first pulse generated by the light flashlamp can be a safety pulse which is smaller than the following pulses. This smaller initial pulse will be safer for the eyes than one large pulse, or series of equally sized pulses. The spacing from the initial pulse to the second pulse can be about 300 ms to allow the blink reflexes (about 250 ms) to protect the eyes from successive pulses.

The system and method provide for multiple pulses of light spaced apart over significant time periods. This allows for a relatively small and inexpensive power supply as compared with prior power supplies used in connection with driving light sources for providing for light treatment of skin. In the system herein the charging circuit has plenty of time to get the capacitive storage element charged back up without complexity and without heating the charging components, and because the discharging circuit and the lamp itself do not have to be aggressively cooled.

Generally light therapy device manufacturers have not offered pulsed light based devices with broadband or blue light due to the complications it can cause. At high peak power and pulse energies, the strong absorption in hemoglobin and melanin can result in large temperature rises of target and associated tissue. Targeting appropriate tissue with broadband or blue pulsed light is made more difficult due to the fact that short wavelength light penetrates tissue shallowly. The result is that epidermal damage is produced with such sources even in the most lightly pigmented skin for single pulse treatments. By multiple pulsing at relatively low fluence/low peak powers and long interpulse spacings, and by using a large spot size, epidermal damage can be minimized and the treatment benefits of broad band or the blue end of pulsed broadband light can be realized. One benefit may be that the follicular stem cells responsible for generating hair are shallowly located in the follicle and can be effectively reached by said broadband pulsed light or even narrow band blue pulsed light during all stages of follicle growth. Epidermal cooling can also increase the safety margin of this device.

Applications which may benefit from pulsed broadband light having appreciable spectral power below 600 nm and above 400 nm include temporary hair removal, hair stunting, delayed hair growth, epidermal pigment removal, temporary or permanent removal or damage of sebaceous glands, the treatment of inflammatory acne vulgaris, reduction of sweat glands or sweat gland function, and the general destruction of follicular stem cells. Such pulsed broadband sources may operate from 400-1200 nm, which includes the 400-550 nm part of flashlamp spectral output generally avoided or filtered out, for the reasons outlined above. Some applications may in fact exclusively use this part of the spectrum, as it is clear from demonstration clinical experiments that this part of the spectrum plays a previously unknown or misunderstood role in dermatologic treatments, particularly in temporary hair reduction. One experiment was performed to study the effect of the blue-green part of the pulsed lamp spectrum. In this experiment, a light source was used to generate low fluence, short pulse operation parameters as described herein. Treatments performed with sub-millisecond pulse durations (in the range of 0.3 ms to 0.5 ms were used), and fluences between 1.7 and 4.0 J/cm$^2$ with multiple pulses (for the 1.7 J/cm^2, the number of pulses was 60, for the 2.5 J/cm^2, the number was 30, and for 4.0 J/cm^2, it was 15), widely spaced in time (in the range of 10 seconds was used) demonstrated that filtering out the spectral band between 350 and 590 nm (while maintaining the overall fluence) results in a greatly reduced efficacy for temporary hair reduction.

Short wavelength (e.g. in the range of 400-600 nm) or broadband (e.g. in the range of 400-1200 nm) hair reduction acts differently than longer wavelength hair reduction (e.g. in the range of 600-1200 nm). These treatments appear to deactivate all the follicles in the treatment area, not just the follicles in a particular hair-growth phase as is the case with longer wavelength devices. Complete and long lasting hair reduction or removal is possible in a single treatment on some individuals. In some individuals this fact allows users to shave only once—just before the first treatment—and prevent the regrowth of hair through maintenance treatments. In two individuals undergoing weekly maintenance treatments, near 100% hair clearance has been observed in excess of 6 weeks from the initial treatment. These treatments are an example of a new method for hair or acne management. In the case of hair, the subject initially shaves, then on a weekly, or even daily basis, is treated or treats himself with low fluences and multiple exposures per treatment area. Using an embodiment of a system and method herein it has been demonstrated that treatments of 3 J/cm^2, with pulse width 0.5-10 ms, of broadband light with wavelengths between 400 and 1200 nm, applied to a particular site 2-10 shots per treatment, for example, can prevent hair regrowth without the need for any shaving beyond the initial session. In the case of acne vulgaris, an initial "knockdown" (e.g. an initial decrease in bacterial population, or decrease in severity or level of infection) of the affected areas may be necessary, followed by regular treatments which serve to maintain a reduced functionality for the sebaceous glands and the bacterial populations that reside in them.

Figure 2:
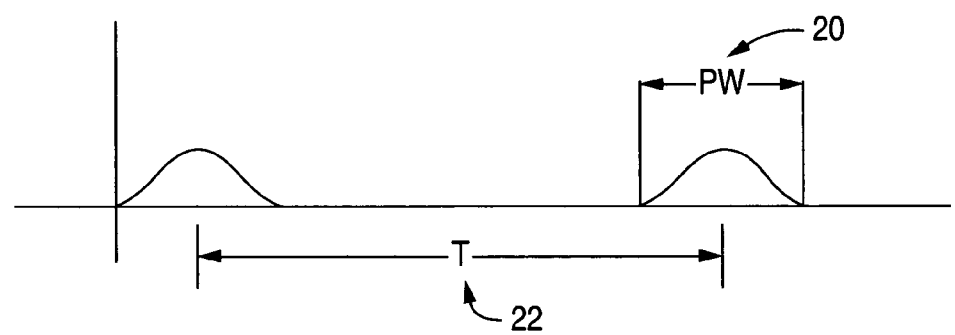
FIG. 2 shows light treatment pulses of an embodiment herein.

FIG. 2 shows treatment pulses provided by an embodiment of the system and method herein. As shown in FIG. 2 a typical pulse can have a pulse width 20 of approximately 1 ms. Depending on the components used in the system as discussed in more detail below the shape and duration of the pulse can vary. Typically the optical energy delivered to skin per pulse will correspond to a fluence range of about 1-6 j/cm$^2$. The time interval 22 between each pulse will typically be in the range of about 1-10 seconds, but in some embodiments the system and method can provide for a separation between pulses of as short as 100 ms.

Fluences as low as 0.1-1.0 J/cm$_2$ may be effective for maintaining hair reduction levels, and for maintaining sebaceous gland reduced function for the treatment of acne and seborrhea. Experiments demonstrating near-100% maintenance of hair reduction on a weekly treatment basis suggest that low fluences (<3 J/cm$^2$) using all of the visible pulsed light spectrum may be effective, and that further, treatments in which only the 400-600 nm part of the pulsed light spectrum is delivered to skin may allow sub-Joule/cm$^2$ fluences to be efficaciously used.

Figure 3:
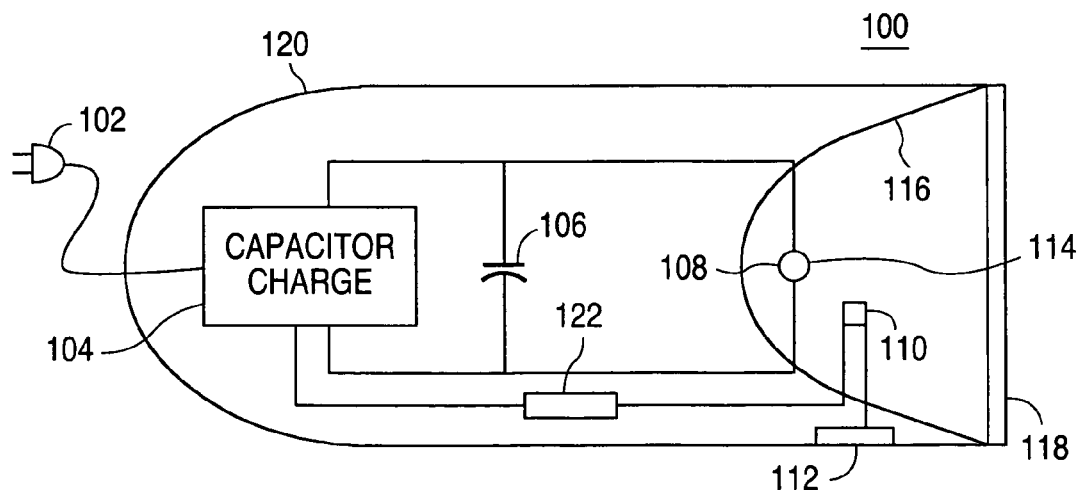
FIG. 3 shows an embodiment of a system herein.

FIG. 3 shows a system of an embodiment of the invention herein. The system includes a housing 120. The housing can be formed in a range of shapes, and with a variety of different materials. Further the housing could be made of a single piece of material or a number of different pieces which are secured together using know techniques. In one embodiment the housing will be formed such that it is ergonomically shaped to facilitate holding the housing and pressing the front window 118 of the system against an area of skin to be treated.

A power cord 102 can be provided to supply AC power to the high power voltage of the system. The AC power can be supplied to a capacitor charging circuit 104. The capacitor charging circuit 104 can use any of a wide range of different designs which are widely known to those of skill in the art. The capacitor charging circuit 104 receives AC power from the power cord 102. The capacitor charging circuit 104 converts the input AC power to a higher voltage DC circuit appropriate for charging the capacitor 106 to a treatment voltage. In one embodiment the capacitor would be of a value in the range of 200-400 µF and would be charged to a treatment voltage of approximately 350 V. In one embodiment the capacitor would be a photoflash capacitor, similar to a capacitor used to drive a flashlamp for a camera, such capacitors are often aluminum electrolytic capacitors, but as one of skill in the art will appreciate a range of different capacitors, or banks of multiple capacitors could be used. The capacitor 106 would discharge a stored charge through the flashlamp 114, and this discharge would cause the flashlamp to output a pulse of light. The discharge of the capacitor 106 is initiated by a trigger 110 which provides an initial triggering event (i.e. supplies, electrical energy) which causes the gas in the flashlamp to become conductive, at which point a charge stored on the capacitor 106 is discharged through the flashlamp. The trigger could be a wire or conducting stripe mounted to the reflector 116, proximal to the lamp body, or it could be a conducting stripe on the lamp etc. As is known in the art a trigger for a flashlamp is in general some electrical device such as a coil, which generates a electromagnetic field in response to a triggering current. The trigger conductor is positioned in proximity to the flashlamp, such that the electromagnetic field energizes the gas in the flashlamp, and causes it to become conductive, such that the charge stored in the capacitor is discharged through the flashlamp. In one embodiment the flashlamp would have a length of about 2 cm, and a 1 cm arc length, and the diameter of the flashlamp would be in the range of 5 mm. The trigger will activate the flashlamp 114 when the capacitor is fully charged and when the window 118 is pressed against the treatment area.

Element 116 is a reflector which reflects light generated by the flashlamp through the window 118 and toward the skin which is pressed against the window 118. The reflector 116 can consist of a molded plastic material covered with a reflective coating, or alternatively may be a stamped sheet metal part covered with a reflective coating.

As shown in FIG. 3, the system can be provided with sensor device 112 which senses when the window is pressed against an area of skin to be treated.

The sensor device could be implemented in number of different ways. One embodiment would provide for a circuit, wherein when the window 118 is physically pressed against the area skin to be treated, the window 118 would be pressed more firmly against the housing 120. The depression of window 118 would close a circuit, wherein when the circuit is initially closed the trigger 110 would be activated, which would cause the gas in the flashlamp 114 to become conductive, and the charged capacitor 106 would be discharged through the flashlamp 114.

The pulse width of the charge discharged through the flashlamp 114, and the result pulse width of the light output by the flashlamp is determined by the characteristics of the flashlamp and the capacitor. The power supply and the trigger can also be coupled to a timing sequence circuit 122 wherein following the initial pulse of the flashlamp, in response to the sensing device determining that the window 118 has been pressed against the skin, the capacitor is charged and then discharged through the flashlamp a predetermined number of times, to apply a treatment to the area of skin adjacent to the window 118. If the sensing device 112 determines that the window 118 has been pulled away from the skin then the sequence of generating pulses of light will stop. In between treatments to different areas a moist sponge or washcloth can be wiped on the window 118 to cool the device.

The system 100 of FIG. 3 would typically be a very low average power system providing a fluence in the range of 1-2 j/cm², and each treatment to an area would provide for a total fluence in the range of 4-20 j/cm². Where the total fluence for a treatment area is determined by the number of pulses applied and the fluence of each individual pulse. In one embodiment of the system 100 the treatment area would be in the range of about 1 cm². With this area the fluence provided by the device is sufficient to provide for temporary removal of hair growth. One embodiment of this device would be very suitable for treating areas of unwanted growth on, or near, facial areas. Because the flashlamp outputs a relatively low amount of energy the flashlamp can be made of relatively inexpensive materials. For example the flashlamp can be a Pyrex-xenon gas flashlamp, where the tube of the flashlamp is made of glass such as Pyrex, hard glass, or boron silicate glass or other relatively inexpensive transparent material. The advantage of using such a material is that it is approximately 80% less expensive than the quartz material used in the high power flashlamps of the prior art. At higher power levels, associated with larger and higher fluence devices, operating with Pyrex type lamp envelope materials would result in a very short lifespan. In one embodiment, the input average power to the lamp would be in the range of 4-5 watts.

In another embodiment, the lamp envelope material may be fabricated from more expensive quartz-based materials, such as cerium-doped quartz, in order to more selectively control the ultraviolet radiation which may otherwise pass to the treatment area.

Another advantage of the system 100 is that because its operation is relatively simple, the device does not need to have a microprocessor. The fact that the device is low average power, its operation is relatively simple, and simplicity of the treatment sensing circuitry all combine to provide a very safe device which does not require microprocessors and sophisticated timing circuits.

Another alternative embodiment of system 100 provide for using a 4 AA batteries to supply power to the capacitor charging circuitry, voltage provided by the batteries would then be converted to the voltage needed to charge the capacitor 106. Because of the low power of the device 100, the window 118 can be made of plastic rather than glass, as is the case in prior higher power systems.

A further embodiment of system 100 uses material for the window 118 which may act as a selective wavelength filter. In the case of a plastic window, said filtering may consist solely of blocking ultraviolet (UV) radiation from the lamp. Alternatively, the window may consist of partially absorbing material which acts to transmit only selected therapeutic spectral bands.

Figure 4:
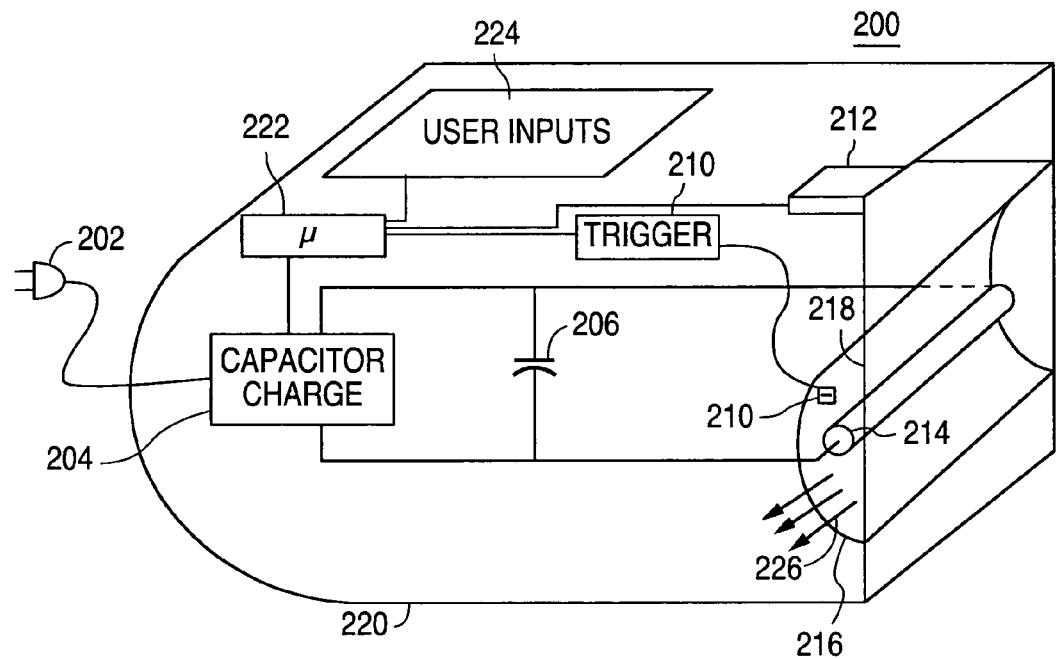
FIG. 4 shows an embodiment of a system herein.

FIG. 4 shows another embodiment of the invention 200. The system 200 includes a number of additional elements that need not be included in the system 100. The system 200 includes a power cord 202 for transmitting AC power to the capacitor charging circuit 204. The capacitor charging circuit operates to charge the capacitor 206. In response the trigger 210 making the flashlamp 214 conductive the charge stored on the capacitor 206 is discharged through the flashlamp 214. A sensor 212 can also be provided to determine when the window 218 is pressed against an area of skin for treatment. The output from the sensor 212 is input to a microprocessor which controls the timing and operation of the system 200. When the microprocessor 222 determines that the window is pressed against the skin and that the capacitor is charged, the microprocessor generates a signal which causes the flashlamp to become conductive, and the charge stored on the capacitor is discharged through the flashlamp 214. The sensing device 212 can be similar to the type of sensing device described above in connection with system 100, or it could be implemented in a number of other ways. For example the sensing device could consist of two electrodes which are placed on a portion of the housing 220, or the window which would be in contact with the skin, when the system is in position for applying a treatment to the skin. A change in the conductivity across the electrodes would be monitored, and when the conductivity matched the conductivity of skin the microprocessor would activate the trigger 210 to apply a pulse of light to the skin. Light generated by the flashlamp 214 would be reflected by the reflector 216 through the window 218 and to the area of skin pressed against the window.

Another type of sensing device may be a capacitance sensor which detects the capacitance of the human body when the device is applied to the treatment area.

Another type of sensor would be an optical sensor that detects the presence of skin at the treatment window.

Another type of sensing device 212 can sense the stray AC electrical field which is present in close proximity to a person's skin, the microprocessor can monitor a signal from the sensing device and when it indicates that the stray AC field is consistent with the sensing device being in close proximity to the skin the microprocessor can fire the trigger. As described above in connection with system 100, the pulse width can be determined by the characteristics of the capacitor 206 and the flashlamp 214. In addition further control circuitry can be provided to further control the pulse width. For example a solid-state device, such as an IGBT, could be connected between one of the electrodes of the flashlamp and ground. The controller can control the opening or the closing of the solid state device, such that the length of time of the charge being discharged through the flashlamp can be controlled in part by the opening and closing of the solid state device. In order to enhance the safety of the system 200 a second controller could be provided which monitors the operation of the controller 222. If the controller 222 fails, then the second controller could either take over the operation of the system 200, and may in some embodiments cause the operation of system to stop operation and generate an error message on the user interface device 224.

In one embodiment of system 200 the area of skin treated (spot size) is about 1 cm². The pulse width of the light generated by the device is in the range of 0.5 to 2 ms. The fluence per pulse is in the range of 4-6 j/cm² and the total fluence applied to a treatment area is in the range of 20-60 j/cm². This higher fluence corresponds to a higher power than provided by the system 100. The system 200 can provide for a wider range of treatments than provided by the system 100. The system 200 can provide treatments for permanent hair reduction or removal, reduction of pigmentation, larger area hair stunting such as the underarm area. Further it should be recognized that the systems herein may also provide for treatment of acne vulgaris and for target sebaceous glands that are associated with acne. It should also be recognized that the treatments provided could include either killing or in some cases stunting tissue growth, or causing to behave different fashion. Generally in the range of 3-6 j/cm² the operation would provide for killing or damaging hair follicles, and would provide for reducing pigment. In the range 1-3 j/cm$^2$ the effect would tend to be more towards arresting hair but very little pigment reduction effect.

The user interface device 224 provides a range of user control. The user interface can display when the system 200 is ready to apply light pulses, and indicate when the device is in standby mode. The user can also put the device into a ready mode or a standby mode. The user interface can also allow the user to apply a treatment by pressing a contact fire button. The user interface can allow the user to adjust the amount of power, or fluence per pulse. The user interface can also provide a beeper to provide information to the user. The user interface can also provide a fan control, and a power level indicator. The power level is such that in the system 200 the flashlamp 214 will be a quartz xenon lamp. In one embodiment the lamp input power will be 20-30 watts. The system 200 can also include a forced air cooling system. In the forced a cooling system a fan not shown will circulate air 226 around the flashlamp 214.

As shown above in systems 100 and 200 the high voltage power supply and the flashlamp are both contained in a relatively small housing of a handheld device. This is in contrast with many prior system which require much more complex and expensive power supply to drive the flashlamp to output much higher levels fluence.

Figure 5A:
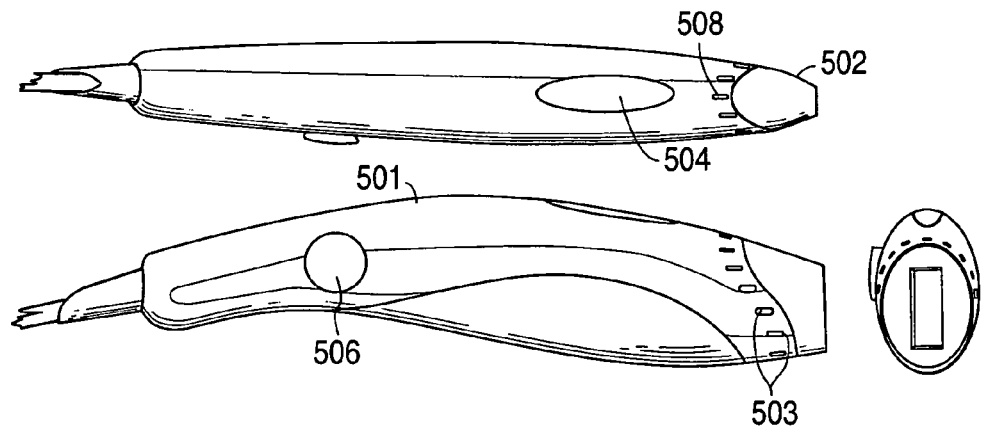
FIG. 5A shows an embodiment of a handpiece housing a flashlamp of a system herein.

Attached hereto as FIG. 5A is a drawing showing one possible configuration for the housing. In this embodiment, the handpiece 501 is provided with a removable front light assembly 502. Cooling vents 503 are located just to the rear of the front assembly. A trigger switch is located at the top center of the Handpiece. An adjustable power control dial 506 is provided to adjust the output energy from the lamp. Finally, an LED 508 is provided to illustrate when the flashlamp had been triggered.

Figure 5B:
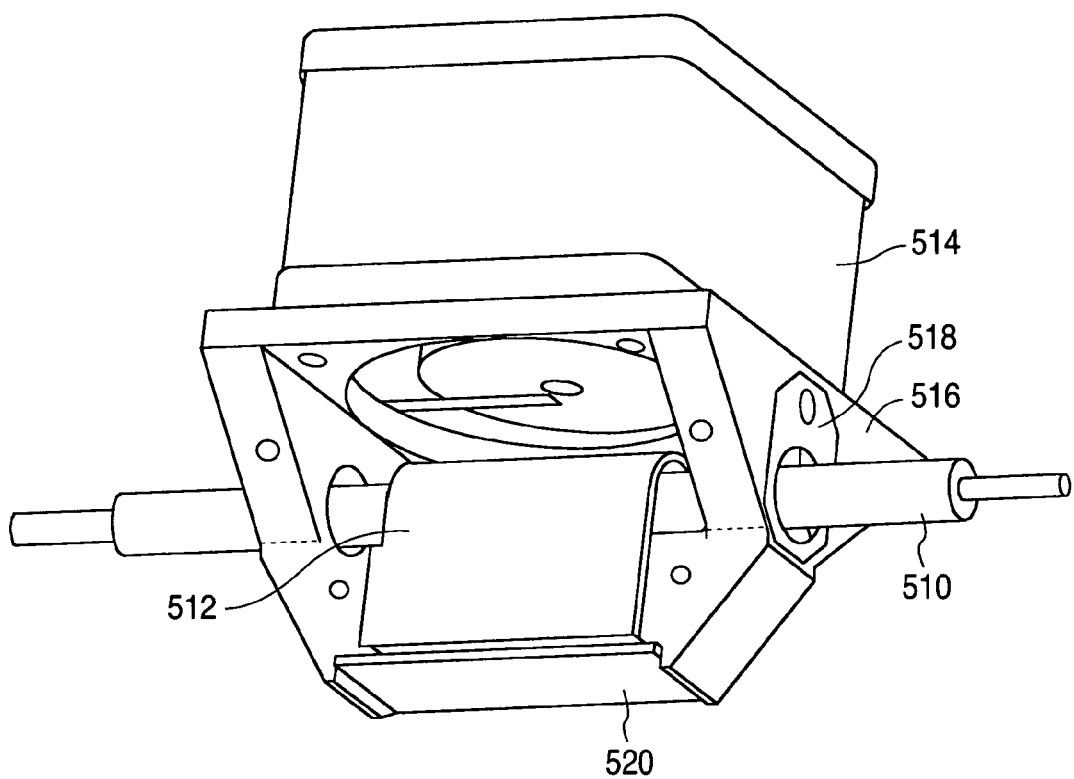
FIG. 5B shows an embodiment of a subsystem with a flashlamp which would be disposed in a handpiece.

FIG. 5B shows the design for a prototype subsystem that has been fabricated for testing and evaluation. The subsystem can include a lamp 510, flashlamp trigger wire (not shown) reflector 512, plastic housing (not shown), and cooling fan 514. The reflector can be a piece of sheet metal with a polished reflective surface. A lamp holding structure 516 is provided, and a bracket 518 couples the lamp 510 relative to the holding structure 516. Additionally, a window 520 is provided. The window 520 can be made of plastic or glass.

In one embodiment, the microprocessor 222 described in connection with FIG. 4, can be a PIC microprocessor. A PIC is a Peripheral Interface Controller—a type of simple microprocessor for which it is relatively simple to write software to control electronic devices. One example of a PIC is Atmel AVR series microprocessor. The PIC microprocessor will run software which (i) monitors users inputs from a user interface, (ii) controls treatment parameters from user inputs, (iii) and monitors safety functions.

In another embodiment which is not shown the system would provide a higher amount of power over a larger treatment area. This requires a larger capacitor to discharge a larger amount of energy through the flashlamp. As a result of the larger energy requirements the components of the power supply will be larger. Thus, in some embodiments it may be desirable to provide the power supply outside of the housing of the hand held device. This high power system can provide treatments for permanent hair reduction, pigment reduction and high speed large area hair stunting. The power supply can be a separate unit which is connected to hand piece with the flashlamp. The power supply would supply power to drive the flashlamp. Controls for the operation of the high power system could be provided on either the hand piece or on the power supply unit. The area of treatment of the high power system can be in the range of 3 cm$^2$. The pulse width for can be in the range 0.1-5 ms. The fluence for this system can be 4-6 j/cm$^2$ per pulse and 20-60 j/cm$^2$ per treatment to a given area. A user interface can provide controls and information to the user such as ready, standby, contact fire, power level, beeper, fan, and power level indicator. A microprocessor/controller would be coupled to the user interface and other components of the system to control the overall operation of the system and to receive information from and provide information to a user. The flashlamp for the high power system could be a quartz xenon lamp. The lamp input power can be in the range of 50-80 watts. The window material for the high power system can be glass. In one embodiment high power system would be water-cooled. In another embodiment it could be air-cooled.

Another embodiment could use a thermally conductive potting material to conduct heat away from the lamp.

Another embodiment which could provide a variation for any of the above systems provides for a replaceable module for the flashlamp of the system. The replaceable module could be implemented in a number of ways. In one embodiment the window which is pressed again the skin would be able to be removed and the flashlamp could be removed from coupling devices which couple the electrodes of the flashlamp to connectors through which the charge from the electrode is received. In another variation the treatment window and the flashlamp could be part of one replacement module. The replacement module could be provided with a plug which is plugged into a receptacle in the handheld device. The charge from the capacitor is then provided through the plug to the electrodes of the flashlamp. One in skilled in the art would recognize that this replaceable module could be implemented in a number of other ways.

Testing has been done which shows that pulses of approximately 1 ms in the range of 5 j/cm$^2$ at a frequency of in the range of 1 hz can provide effective treatment for removal of hair and pigments. In one test application of 5 J/cm$^2$ pulses at 1 Hz and in the range of 5 pulses provided both hair removal and pigment treatment. Such testing suggests that different skin types can benefit from different types of filtering. For example for light skin very little filtering is advantageous. Testing has also shown that it is advantageous to build a thermal pedestal at the treatment area. This means it is beneficial to allow the heat to build up at the treatment area through an accumulation of pulses from the flashlamp. In some application it may also be possible to achieve significant vascular effects.

Treatments for acne vulgaris using low fluence, multiple exposure, broadband pulsed light have been described above. However, it may be useful to shift the spectral shape of the light source. Some evidence has been recently presented suggesting that yellow-green light from pulsed dye lasers used at sub-purpuric fluences (up to ~3 J/cm$^2$) may be useful in the treatment of acne either directly ("*Efficacy of low-fluence pulsed laser in treatment of inflammatory acne vulgaris: a randomized controlled study*", E D Seaton et alia, poster session at the American Academy of Dermatology, March 2003, which is incorporated by reference herein), or. in conjunction with photosensitizing agents ("*Treatment of acne vulgaris with laser-assisted photodynamic therapy*", M R Alexiades-Armenakas et alia, presentation at the American Society for Lasers in Dermatology and Medicine, April 2003, which is incorporated by reference herein). Operating low fluence broadband flashlamps for these treatments may allow for similar results with greatly reduced cost and complexity of the light-based device. It has been suggested that the specific waveband associated with pulsed dye laser treatments may be key for acne treatments. Wavelength shifting of the broadband output using fluorophores and phosphors can produce efficient yellow-green output in the 1 J/cm$^2$ range, comparable with the PDL treatment parameters reported for acne treatment. An example material is 0.1-1.0% cerium-doped YAG crystals used as a filter. The 400-500 nm band emitted from the flashlamp would be converted to 500-650 nm light.

Still another application is the treatment of fine vasculature, diffuse redness and persistent erythema. The pulsed light bands from 400-600 nm are particularly important for these treatments since hemoglobin absorption is strong in this region. The short (millisecond) range pulses should be effective in targeting the small scale vascular structures associated with these conditions. Repeated small fluence exposure treatments will be required to produce the same clinical effects seen with large single pulse treatments using pulsed and filtered flashlamp light sources in prior devices.

Figure 6:
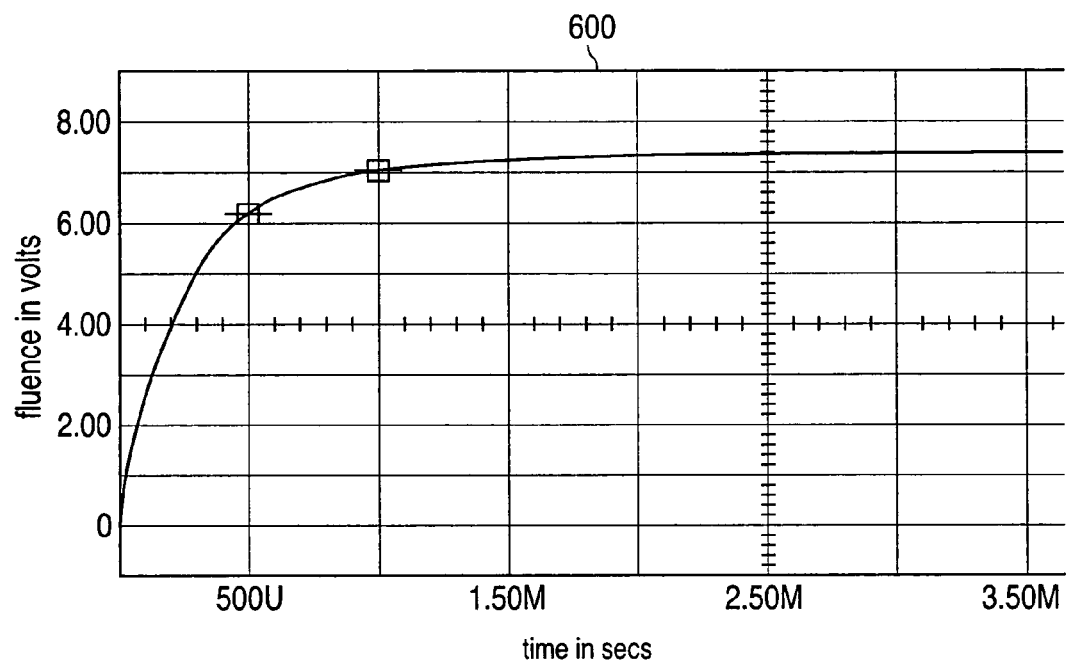
FIG. 6 shows a modeled output of the fluence for a light pulse of an embodiment herein.
Figure 7:
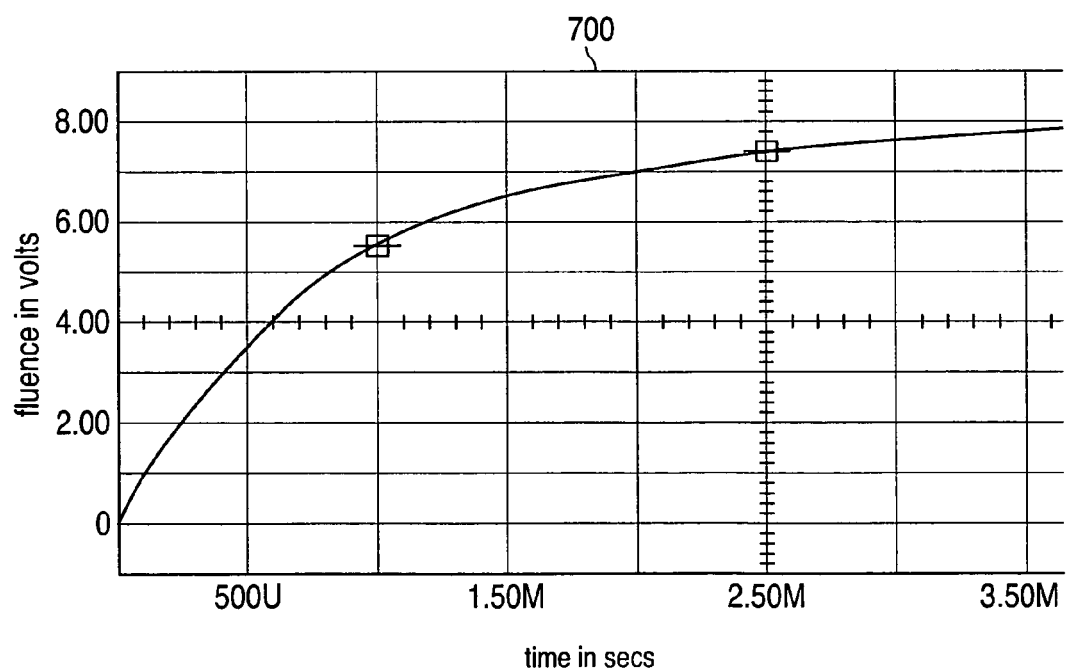
FIG. 7 shows a modeled output of the fluence for a light pulse of an alternative embodiment herein.

FIGS. 6 and 7 illustrate aspects of the operation of embodiments herein. FIGS. 6 and 7 show graphs 600 and 700 with accumulated fluence over time for a pulse of light output by a system. The vertical axis shows the accumulated energy or fluence on the skin versus time on the horizontal axis. These graphs show simulated fluence for different values for the capacitor, and the impedance of the flashlamp. For the simulations shown in 600 and 700 the charging voltage on the capacitance was 350 volts and the modeled resistance of the components and connections between the capacitor and flashlamp was not varied for the modeling the shown in graphs 600 and 700. The value of the capacitance for the modeling of graph 600 was 100 µF and valued of the impedance (Ko) for the flashlamp was 6, the area of the spot size was 1 cm$^2$. The value of the capacitance for the modeling shown in 700 was 300 µF, the impedance of the flashlamp was 7.67 and the area was 3 cm$^2$. These graphs show that different embodiments of the system herein provide for different characteristics of the output fluence. In the case of the modeling shown in 600 it can be seen that after approximately 1.5 ms the output light pulse provides little appreciable addition of energy, whereas the modeling of graph 700 shows that light pulse continues provide an appreciable amount of energy after 1.5 ms and up to about 2.5 ms. These graphs illustrate that different capacitors and lamps maybe used, and gives an indication of the shape of the pulse width and energy delivery, for the types of systems described above.

There are a wide range of different possible embodiments for systems herein. For example one type of system could be provided for hair stunting treatments on small areas of skin. A simple inexpensive handheld device for this type of system would provide a spot size (treatment area) of about 1 cm$^2$. The capacitor and flashlamp would provide a fixed pulse width of between around 0.5 to 2 ms. The fluence per pulse would be about 1-2 J/cm$^2$, and a treatment application for an area would apply multiple pulses to provide an energy of about 4-10 J/cm$^2$ per treatment. This system would provide a contact fire switch. The lamp type would be xenon filled pyrex envelop, and the lamp input power would be 4-5 watts. In this simple system no microprocessor would be required. The power source could provide a user with the option of using 4 AA alkaline batteries, or using a power adapter to receive 120 V AC power. The lamp cooling could be convection air or conduction, and water and/or ice could optionally be used. The treatment window could be cooled using a wet sponge or washcloth, or optionally ice. Given the low energy and low cost requirements of the system a plastic treatment window would be used.

Another system herein could be provided for hair stunting treatments on larger areas of skin, and for larger diameter follicles, and would provide a larger spot size than that described in the system above. For example, in one embodiment the spot size would be about 3 cm$^2$. The capacitor and flashlamp would provide a fixed pulse width of between around 2 to 3 ms. The fluence per pulse would be about 1-2 J/cm$^2$, and a treatment application for an area would apply multiple pulses to provide an energy of about 4-10 J/cm$^2$ per treatment. This system would provide a contact fire switch. The lamp type would be pyrex envelope filled with a xenon gas, and the lamp input average power would be about 20 watts. In this simple system no microprocessor would be required. The power source could be either a power adapter to receive 120 V AC power, or an AC cord with power adapter built into the handpiece could be used. The lamp cooling could be forced air or conduction to potting material. The treatment window could be cooled using a wet sponge or washcloth, or optionally ice. Given the low energy and low cost of the system a plastic or glass treatment window would be used.

Another embodiment of a system herein provides for permanent hair reduction, pigment reduction and stunting growth of larger diameter hair. This system is a handheld device. The spot size is in the range of 1 cm$^2$. The pulse width is in the range of 0.5-2.0 ms. The fluence per pulse would be about 4-6 J/cm$^2$, and a treatment application for an area would apply multiple pulses to provide an energy of about 30-60 J/cm$^2$ per treatment. Due to the higher power and possible broader range of applications, additional controls may be desired, such as user interface which indicates when the device is in a ready mode, or stand by mode. The power level output can be adjusted by varying the voltage on the capacitor, and a power level indicator can be provided. The lamp type is quartz envelope filled with a xenon gas. The lamp input power is 20-30 watts. This system would be provided with a main controller and back up controller to provide for enhanced safety of operation due to the issues associated with providing for variable power control, and possible clinical risks associate with higher energy pulses, particularly for darker skin types. The power supply can provide for using an ac power cord. The lamp cooling is provided using forced air. Window cooling is provided using wet sponge of towlette. The window material is preferably glass, but for lower power operation plastic could be used.

Another embodiment of a system herein provides for permanent hair reduction, pigment reduction and high speed large area hair stunting. This system, due to its higher power of operation, would likely be implemented using a handpiece which houses the flashlamp, and the power supply could be implemented in a separate console which would be connected to the handpiece and the flashlamp via a umbilical cable carrying control signals and power. The spot size for the system would be in the range of 3 cm$^2$. The pulse width would be fixed somewhere in the range of 2-5 ms. The fluence per pulse would be about 4-6 J/cm$^2$, and a treatment application for an area would appl multiple pulses to provide an energy of about 30-60 J/cm$^2$ per treatment. Due to the higher power and possible broader range of applications, additional controls may be desired, such as a user interface which indicates when the device is in a ready mode, or in a stand by mode. The power level output can be adjusted by varying the voltage on the capacitor, and a power level indicator can be provided. The lamp type is quartz envelope filled with a xenon gas. The lamp input average power is 50-80 watts. This system would be provided with a main controller and back up controller to provide for enhanced safety of operation due to the issues associated with providing for variable power control, and possible risks associate with higher energy pulses. The power supply can be provided for using a ac power cord. The lamp cooling is provided using forced air, and window which is in contact with skin, and through which light is transmitted, can be cooled by application of an wet cloth, or antiseptic towlette. The window material is preferably glass.

In considering different implementations of the method and system herein it is constructive to consider a number of different combinations and operations which can be provided in different embodiments of such a system or method. Below is an illustrative, but non-exhaustive identification of some combinations, which could be utilized in accordance with the present system and method.

A Broad band 400-1200 nm multiple pulse light treatment using a light source with pulse spacing greater than 100 ms and less than 15 seconds between each pulse, where multiple pulses are applied to each treatment spot.

A Blue band 400 nm-550 nm light source for dermatologic treatment for applying light treatments to skin.

A dermatologic treatment device with lamp current waveshape determined primarily by capacitor and lamp characteristic.

A dermatologic treatment device with lamp current waveshape determined primarily by the impedance of the storage capacitor, lamp and an inductor (coil) circuit.

A dermatologic treatment device in which the energy for the treatment pulse is stored in a capacitor in a handpiece, which also holds a light source for applying the treatment.

A dermatologic treatment device with broadband fluence 400-1200 nm from 0.5-8 j/cm^2 in each pulse and delivering from 2-50 pulses per treatment spot.

A dermatologic treatment device with 400-600 nm fluence from $0.1-5$ j/cm$^2$ in each pulse and delivering from 2-50 pulses per treatment spot.

A dermatologic treatment device with capacitive contact sensor to prevent treatment when window is not in contact with the skin.

A dermatologic treatment device with multiple capacitive contact sensors.

A dermatologic treatment device with mechanical contact sensor to prevent treatment when window is not in contact with the skin.

A dermatologic treatment device with multiple mechanical contact sensors A dermatologic treatment device with resistive contact sensor to prevent treatment when window is not in contact with the skin.

A dermatologic treatment device with multiple resistive contact sensors A dermatologic treatment device with stray field contact sensor to prevent treatment when window is not in contact with the skin.

A dermatologic treatment device with multiple stray field contact sensors.

A dermatologic treatment device with contact sensors that must "break and make" between single site/multi-pulse treatments to ensure that the user moves to the next treatment site. This means that the contact sensors must first indicate contact with the skin prior to enabling the firing sequence of light pulses, and before the NEXT sequence can begin, the sensors must change state, indicating that the device is no longer in contact with the skin.

A multiple pulse dernatologic treatment device that emits a smaller initial light pulse in a treatment sequence A multiple pulse dermatologic treatment device that emits a series of increasingly larger pulses as part of treatment sequence.

A multiple pulse dermatologic treatment device that has cooling cryo chilled contact window, gel, forced air, to protect the epidermal pigment during a treatment. The cryo can be a cryogen—liquid or gas used to cool an object. In one embodiment this can be a compressed/refrigerated liquid is sprayed on skin. As the liquid strikes the skin, it absorbs heat and cools the epidermis, and to some extent, the dermis.

A dermatologic treatment device with optical sensors to measure quantity or quality of reflected light from treatment area to determine the appropriate treatment parameters for that area.

A multiple pulse dermatologic treatment device with a lamp, reflector and a filter which cuts of radiation below 400 nm.

A multiple pulsed dermatologic treatment device with wavelength output from 400 nm-600 nm.

A multiple pulsed dermatologic treatment device with wavelength output from 400 nm-1200 nm.

A multiple pulsed dermatologic treatment device with wavelength output from 400 nm-500 nm.

A dermatologic treatment where a first pulse is small, and reflection is sensed by a detector, if the reflection is too small or too large then the following pulses in the sequence are inhibited. (providing eye safety).

A dermatologic treatment where a first pulse is small, and reflection is sensed by a detector, the following pulse or pulses are modified based upon the measured reflected light. (for safety and efficacy).

A dermatologic treatment device that consists of a lamp, reflector, filter, and that applies 2 or more pulses to the treatment area with pulse spacing and pulse width such that it causes multiple thermal excursions of the target tissue resulting in the destruction of the target by repeated temperature cycles.

While the above description provides details for a number of embodiments herein, it should be recognized that other possible modifications and variations are possible, and that other systems and methods not expressly described above are still within the scope of the present invention. Thus, the scope of the inventions are defined by the attached claims and their equivalents.

What is claimed is:

1. A method of treating a treatment area of skin to reduce hair regrowth with light energy comprising the steps of:
    shaving hair follicles within the treatment area;
    thereafter, generating between two and ten pulses of light, each pulse having pulse width between approximately 0.1 ms to 3 ms, and a fluence between 1.0 and 3.0 joules/cm$^2$ and having time period of greater than 0.5 seconds and less than 3 seconds between pulses; and
    applying the pulses of light to the treatment area to arrest, stunt or retard hair regrowth.

2. The method of claim 1, further comprising:
    generating a safety pulse of light at least approximately 300 ms prior to the generating pulses of light.

3. The method of claim 1, further comprising:
    wherein the applying of light pulses to the treatment area, includes transmitting the pulses of light through a treatment window, and
    sensing the presence of a patient's skin at the treatment window prior to generating the pulses of light.

4. The method of claim 1, wherein the pulses of light applied to the treatment area include light energy in the range of approximately 400 nm to 600 nm.

5. The method of claim 1, wherein the pulses of light applied to the treatment area include light energy in the range of approximately 400 nm to 1200 nm.

6. The method of claim 1, wherein the pulses of light applied to the treatment area have a spot size of at least approximately 1 cm$^2$.

7. The method of claim 1, wherein each pulse of light applied to the treatment area has a fluence in the range of approximately 1-2 J/cm$^2$.

8. A method of treating a treatment area of skin with light energy to reduce hair regrowth comprising the steps of:

shaving hair follicles within the treatment area;

thereafter, generating pulses of light having pulse width between approximately 0.1 ms to 3 ms, and having time period of greater than 0.5 seconds and less than 3 seconds between pulses;

applying the pulses of light to the treatment area;

wherein the applying the pulses of light to the treatment area, includes transmitting the pulses of light through a treatment window;

sensing the presence of a patient's skin at the treatment window prior to generating the pulses of light;

wherein the pulses of light applied to the treatment area includes light energy in the range of approximately 400 nm to 600 nm;

wherein the applying the pulses of light to the treatment area includes applying in the range of approximately two and ten pulses of light to the treatment area; and wherein the pulses of light applied to the treatment area have a fluence of between 1.0 and 3.0 joules/cm$^2$ to arrest, stunt or retard hair regrowth.

* * * * *